United States Patent
Makower et al.

(10) Patent No.: US 6,283,983 B1
(45) Date of Patent: Sep. 4, 2001

(54) PERCUTANEOUS IN-SITU CORONARY BYPASS METHOD AND APPARATUS

(75) Inventors: Joshua Makower, Los Altos, CA (US); Robert S. Schwartz; David R. Holmes, both of Rochester, MN (US); Robert A. Van Tassel, Excelsior, MN (US)

(73) Assignee: TransVascular, Inc., Menlo Park, CA (US)

( * ) Notice: Subject to any disclaimer, the term of this patent is extended or adjusted under 35 U.S.C. 154(b) by 0 days.

(21) Appl. No.: 09/192,554

(22) Filed: Aug. 10, 1998

Related U.S. Application Data

(63) Continuation-in-part of application No. 08/730,496, filed on Oct. 11, 1996, now Pat. No. 5,830,222
(60) Provisional application No. 60/005,164, filed on Oct. 13, 1995.

(51) Int. Cl.$^7$ .................................................. A61M 29/00
(52) U.S. Cl. ........................ 606/198; 606/108; 623/1.13
(58) Field of Search .............................. 606/1, 108, 192, 606/194, 195, 198, 200; 623/1, 12, 1.11, 1.13, 1.14; 604/96

(56) References Cited

U.S. PATENT DOCUMENTS 5,064,435 * 11/1991 Porter ..................................... 606/198
5,797,920 * 8/1998 Kim ....................................... 606/108
5,830,222   11/1998 Makower .

FOREIGN PATENT DOCUMENTS

| 9713463 | 4/1997 | (WO) . |
| 9713471 | 4/1997 | (WO) . |
| 9727893 | 8/1997 | (WO) . |
| 9727897 | 8/1997 | (WO) . |
| 9727898 | 8/1997 | (WO) . |
| 9808456 | 3/1998 | (WO) . |
| 9846115 | 10/1998 | (WO) . |
| 9846119 | 10/1998 | (WO) . |

* cited by examiner

*Primary Examiner*—Michael Buiz
*Assistant Examiner*—William W. Lewis
(74) *Attorney, Agent, or Firm*—Robert D. Buyan; Stout, Uxa, Buyan & Mullins, LLP

(57) ABSTRACT

Methods and devices for percutaneous, in situ coronary bypass wherein a tissue puncturing catheter is used to form blood flow paths between an artery and an adjacent vein such that arterial blood will flow through a segment of the adjacent vein, thereby bypassing a lesion in the artery. The tissue puncturing catheter comprises a flexible catheter having a tissue puncturing apparatus such as a sharp tipped member, an electro-surgical apparatus or a laser beam passable therefrom to create the desired blood flow paths between the artery and vein. Stents are provided for facilitating blood flow through the blood flow paths and the segment of the vein used as the bypass conduit. One such stent is specially constructed to carry arterial blood in one direction through the vein segment while allowing venous blood to continue to flow in the opposite direction through that venous segment.

16 Claims, 4 Drawing Sheets

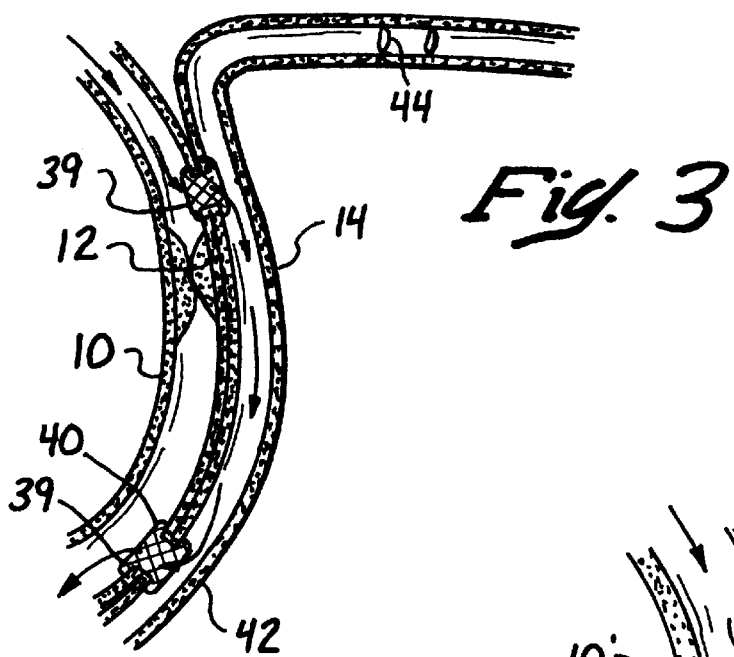
Fig. 3
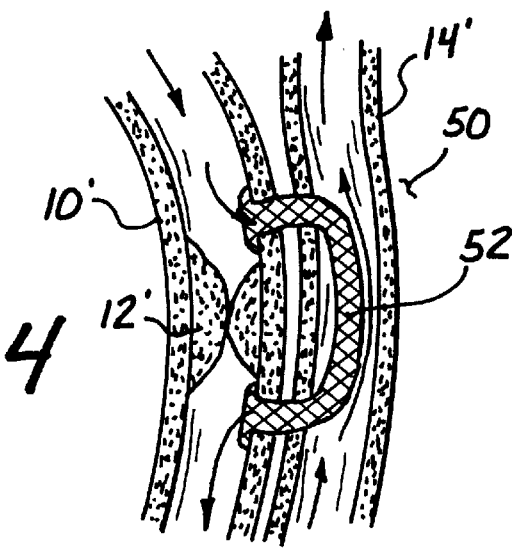
Fig. 4
Fig. 5
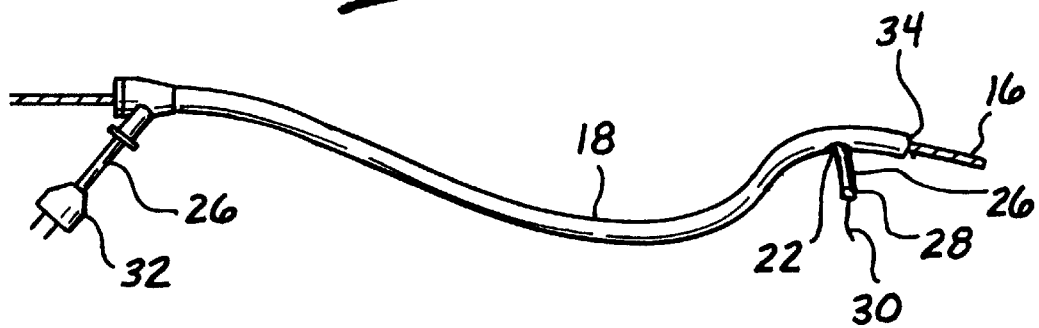

PERCUTANEOUS IN-SITU CORONARY BYPASS METHOD AND APPARATUS

RELATED APPLICATION

This application is a continuation-in-part of application Ser. No. 08/730,496 entitled Method for Interstitial Transvascular Intervention (as amended), filed on Oct. 11, 1996, now U.S. Pat. No. 5,830 222 with a claim of priority to provisional application 60/005,164 filed on Oct. 13, 1995. The entire disclosure of such related patent application is expressly incorporated herein by reference.

BACKGROUND OF THE INVENTION

I. Field of the Invention

This invention relates generally to myocardial revascularization cardiac surgery, and more particularly to an improved method and apparatus for performing coronary lesion bypass to restore patency to blocked coronary or stenotic arteries.

II. Discussion of the Prior Art

Coronary artery disease is a major cause of death in the United States. The disease results in the build-up of calcified, fibrous and fatty deposits on the walls of the coronary arteries supplying blood to the myocardium. The narrowing of one or more cardiac arteries often results in ischemia, leading to angina pain. Moreover, clots may result in blockage of the flow of blood through a blood vessel that has been narrowed by the stenotic lesion, resulting in myocardial infarction or unstable angina.

One approach for restoring patency to a narrowed coronary artery is commonly referred to as "balloon angioplasty". Here, a catheter having an inflatable expanding member on its distal end is routed through the vascular system until the yet uninflated member is juxtaposed with the lesion to be treated. Saline and/or contrast is then introduced through a lumen in the catheter to the interior of the expander member with sufficient pressure to inflate the expander member and fracture or compress the lesion into the wall of the blood vessel. When the expander member is deflated and the catheter removed from the patient, patency is restored to the affected coronary artery.

Not all patients suffering from coronary artery disease are candidates for balloon angioplasty. A significantly more invasive procedure, commonly referred to as coronary bypass surgery, may then be called for. In this procedure, the sternum is divided and retractors are used to expose the chest cavity. The pericardial sack is opened and the patient is placed on a heart/lung machine, allowing the patient's own heart to be stopped. A vascular segment, which may be harvested from the patient's saphenous vein or the internal mammary or radial artery, is then anastomosed to the blocked artery beyond the point of obstruction to thereby provide a shunt blood path along that lesion. Once the necessary bypass segment(s) have been sutured in place, the heart is then restarted, the chest wall is reanastomosed together and the surgical incision closed.

Such coronary bypass surgery is not only quite expensive in terms of medical costs, but also in terms of the relatively lengthy time required for recuperation.

A need exists for a less traumatic coronary bypass procedure. Some medical centers have recently reported on minimally invasive surgery wherein the bypass procedure is conducted through a relatively small wound in the chest and rib cage, with drugs being given to slow the heart rate. At this point, however, such a procedure is not widely practiced and can only be performed in selective cases where reasonable access can be had to the coronary artery containing the stenotic lesion.

A real need exists for a catheter based procedure for performing coronary bypass in those cases where balloon angioplasty is determined to be ineffective. It is the principal purpose or object of the present invention to provide such a new technique as well as instruments and devices for carrying out the procedure.

SUMMARY OF THE INVENTION

We have developed a procedure which we call "percutaneous in-situ bypass surgery" which will be referred by the acronym, PIBS. Referring to FIGS. 1 and 2, which respectively show the anterior and posterior view of a human heart, it can be noted that the major coronary arteries and branches thereof are physically located in close and generally parallel proximity to corresponding venous structures. Thus, with reference to FIG. 1, the left anterior descending coronary artery runs generally parallel with the anterior descending vein of the heart across the left ventricle and, similarly, in FIG. 2, the right coronary artery is closely juxtaposed to the small veins of the heart. The posterior interventricular branch of the right coronary artery extends generally parallel to the middle vein of the heart on the posterior side of the right ventricle. The circumflex branch of the left coronary artery generally underlies the great vein of the heart.

The fundamental principle involved in the PIBS procedure of the present invention is to utilize a coronary vein as a conduit, either to convey arterial blood directly around an arterial stenosis or occlusion or to use the vein as a chamber in which to place an arterial conduit, such as a tubular stent, and where the procedure can be performed entirely percutaneously.

In accordance with one aspect of the invention, the coronary artery is connected to the neighboring vein proximal to a stenosis or occlusion and the vein is then reconnected to the affected artery distal to the occlusion. In carrying out the method, an elongated instrument, much like a conventional guide wire, is routed through the vascular system and through the ostium of the stenosed artery until the tip thereof is proximal to the lesion to be bypassed. Either the guide wire itself or an instrument carried by the guide wire may be used to pierce through the artery wall and through a wall of the neighboring vein. A stent delivery catheter is then routed over the guide wire until the tubular stent bridges the surgically created openings in the artery and vein and the stent is deployed at this point to create a blood impervious channel. The guide wire may then be advanced down the vein to a location distal of the arterial blockage and, again, the guide wire or another instrument is deployed over the guide wire to puncture through the vein wall and the neighboring arterial wall. Again, a second stent is then inserted to anastomose the opening in the vein and the opening in the artery. As a result, a blood flow path is created from the artery through the vein segment bypassing the lesion in the artery and then back into the artery distal of the blockage. A blocking stent may be placed in the coronary vein proximal to the anastomosis to prevent arterial blood flow back to the right ventricle via the coronary sinus.

In accordance with a closely related procedure, a vein segment is again used as a conduit but, in this case, the vein merely serves as a conduit for an arterial graft. In accordance with this second procedure, the artery is entered, a hole is again made through the artery wall and through the neighboring vein wall using a percutaneous approach with the piercing instrument also being used to puncture through the vein wall and the neighboring arterial wall at a location distal of the blockage. An elongated stent having its proximal end in the artery and extending through the first puncture wounds and through the lumen of the neighboring vein and its distal end extending through the puncture in the vein and into the neighboring artery, provides a bypass path for arterial blood flow.

The stent(s) may be either of the self-expanding type or a stent delivery catheter preferably having two balloon expanders thereon for expanding the proximal and distal stents may be utilized. To enhance the compatibility of the stent or stents employed with the adjacent natural tissue and with blood, they may first be covered with a blood impervious layer. Then, by using novel materials technology, endothelialization of both surfaces of the stent conduit can occur and will develop and maintain both a neointimal lining and an external endothelium as well.

Another special instrument to be used in carrying out the method of the present invention resides in a catheter to be used in placing the puncturing instrument at the desired locations proximal to and distal to the lesion being bypassed. The guiding catheter may have two lumens, a central lumen capable of accepting a standard guide wire and a second carrying the wire for piercing through the blood vessel walls. The piercing instrument may include a mechanical cutting device on its distal end or, alternatively, may comprise an electrosurgical electrode or a laser beam directed through an optical fiber, either of which can be used to burn through the blood vessel walls.

DESCRIPTION OF THE DRAWINGS

FIG. 3 is a greatly enlarged view of a portion of a coronary artery and an associated vein helpful in understanding the method of the present invention in accordance with a first procedure;

FIG. 4 is a view similar to FIG. 3 helpful in understanding the method of the present invention in accordance with an alternative procedure;

FIG. 5 is a perspective view of a guide catheter, guide wire and blood vessel puncturing instrument for use in carrying out the method of the present invention;

DESCRIPTION OF THE PREFERRED EMBODIMENT

Figure 6:
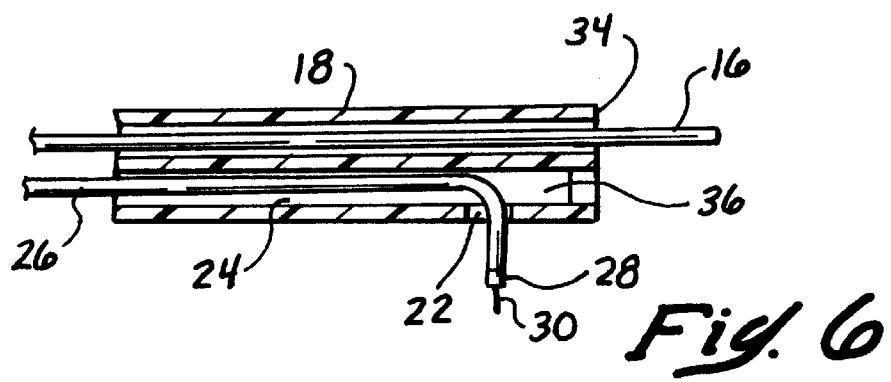
FIG. 6 is a cross-sectional view of the distal end portion of the instrument of FIG. 5.
Figure 11:
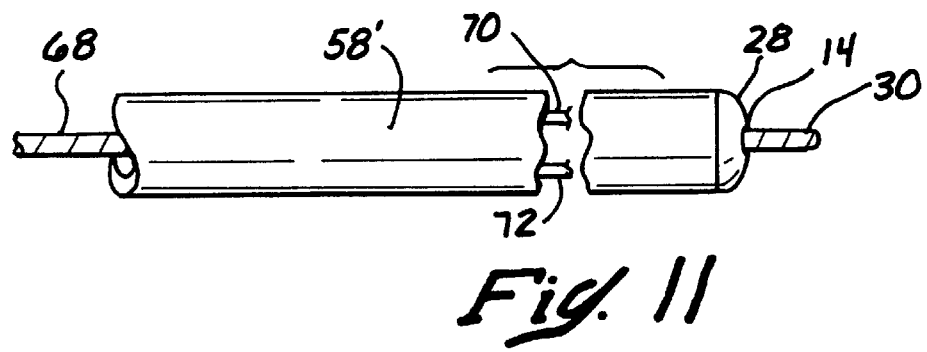
FIG. 11 is a partial side elevation view of another instrument useful in carrying out the method of the present invention.

Referring first to FIG. 3, an explanation will be given of the PIBS procedure of the present invention in accordance with a first procedure. There is shown in cross section a greatly enlarged section of a coronary artery 10 that is substantially blocked by a stenotic lesion 12. Located closely adjacent the arterial segment 10 is a venous segment 14. To percutaneously bypass the stenotic lesion 12, a catheter-like instrument, such as is shown in FIGS. 5 and 6, is used. It is designed to be introduced into the vascular system using the Seldinger technique. First, a radiopaque guide wire 16 is fed through an introducer and advanced through the vascular system and through the coronary ostium until the distal end of the guide wire 16 approaches the stenotic lesion 12 proximally thereof. The guide wire, being radiopaque can readily be viewed on a fluoroscope. Next, a guide catheter 18 may be fed over the proximal end of the guide wire and advanced there along. The guide catheter 18 has a side exit port 22 located a predetermined distance proximal of the distal end thereof connected to an internal lumen 24 (FIG. 11). A working catheter 26, which may comprise an electrosurgical device having either monopolar or bipolar electrode(s) as at 28 and 30 at its distal end, is-retracted so that the distal end portion thereof is fully contained within the lumen 24 as the guiding catheter 18 is being advanced over the guide wire 16. The working catheter 26 has a plug 32 at its proximal end which is adapted to be connected to terminals of an electrosurgical generator (not shown). An optical fiber driven by an external laser may also be used. Once the distal end 34 of the guiding catheter 18 is brought into close engagement with the proximal side of the stenotic lesion 12, the working catheter 26 may be advanced in the distal direction such that the distal electrodes 28 and 30 come into engagement with a diverter plug 36 placed in the lumen 24 just distal of the exit port 22. The diverter plug causes the distal end of the working catheter 26 to exit the port 22 at generally a right angle of the longitudinal axis of the catheter. When it is brought into contact with the inside wall of the artery 10 and the electrosurgical generator is actuated, the needle electrode 30 will cooperate with the electrode 28 as a bipolar pair and will effectively ablate the arterial wall and through the wall of the adjacent vein 14. Persons skilled in the art can appreciate that the electrosurgical vessel puncturing device may be monopolar and that a laser feeding it energy through a long, flexible optical fiber can also be used to effect the openings formed in the atrial and venous walls.

Following the formation of openings in the artery wall and vein wall at the site proximal to the stenotic lesion, the guiding catheter 18 can be advanced through the openings thus formed until the exit port 22 is located just distal of the stenotic lesion. Suitable radiopaque marking bands, as at 38, disposed about the exit port 22 serve to locate the exit port when viewed fluoroscopically. The procedure is repeated with the electrosurgical catheter 26 being again advanced so that its distal end exits the port 22, whereupon the electrosurgical generator is again activated to create a sufficient RF voltage between the needle electrode 30 and the return electrode 28 to penetrate through the venous wall and then through the arterial wall.

Figure 7:
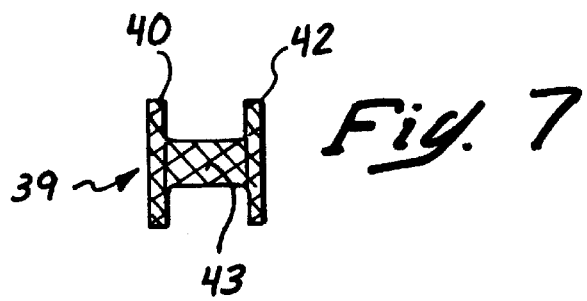
FIG. 7 is a side elevation view of a cuff link stent.
Figure 8:
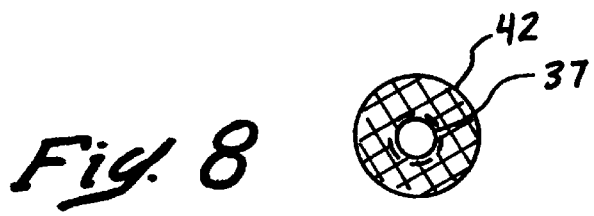
FIG. 8 is a side view of the stent of FIG. 7.

At this point, the electrosurgical catheter 26 (or laser fiber as the case may be) may be stripped out from the lumen 24 and replaced with a conventional stent delivery catheter carrying a pair of self-expanding "cuff-link" stents, such as depicted in FIGS. 7 and 8 of the drawings. The tubular stent 39 is preferably a self-expandable, double disk device made from braided stainless steel or Nitinol wire, the two disks 40 and 42 being linked together by a short tubular connecting waist 43 corresponding to the size of the surgically created openings in the wall of the artery 10 and the vein 14. The diameter of the disks 40 and 42 may be about 3–5 mm and the lumen 37 thereof may have a diameter of about 2–4 mm. The lap or flange on the proximal and distal ends of the stent prevent it from migrating with blood flow into the vein. The stent material preferably has a three-dimensional nature, permitting marked tissue ingrowth so that the neointima can support the connection without developing stenosis. The stent material also has non-porous, impermeable sides to prevent stenotic AV connections. The porosity of the covered stent material is important to permit tissue ingrowth for anchoring within a relatively short time period.

Typically, for delivery, the stent of FIG. 7 will be stretched longitudinally sufficiently so that the disk-like end portions 40 and 42 will be of a sufficiently reduced diameter so as to fit within the lumen of a 6–8 Fr. delivery catheter. Upon advancement of the stent out from the distal end of the delivery catheter, it will assume a shape like that of FIG. 7 due to the memory property of the Nitinol wire from which the stent is initially braided.

If non-self-expanding stents are employed, such as covered Palmaz stents, then the stent delivery catheter will include one or more balloons at the distal end thereof with the yet unexpanded stent(s) fitted over the balloon(s). The stent delivery catheter may then be steered so that the stent spans the distance between the artery and the vein to be anastomosed. Inflation of the balloon will then radially expand the stent to lodge it in place. With this arrangement, the balloons may be on the exterior of either the guide 18 or the cutting catheter 26 which then also function as the stent delivery device.

When the stent delivery catheter (not shown) has been advanced through the lumen 24 of the guide catheter 18sufficiently far to engage the diverter plug 36, its distal end will be directed normal to the longitudinal axis of the guide catheter 18. Now, when the stent device of FIGS. 7 and 8 has been inserted through the openings formed through the venous and arterial walls, the stent will be deployed, such that the flared end portions 40 and 42, respectively, reside in the lumen of the vein 14 and the lumen of the artery 10 as shown in FIG. 3.

Figure 1:
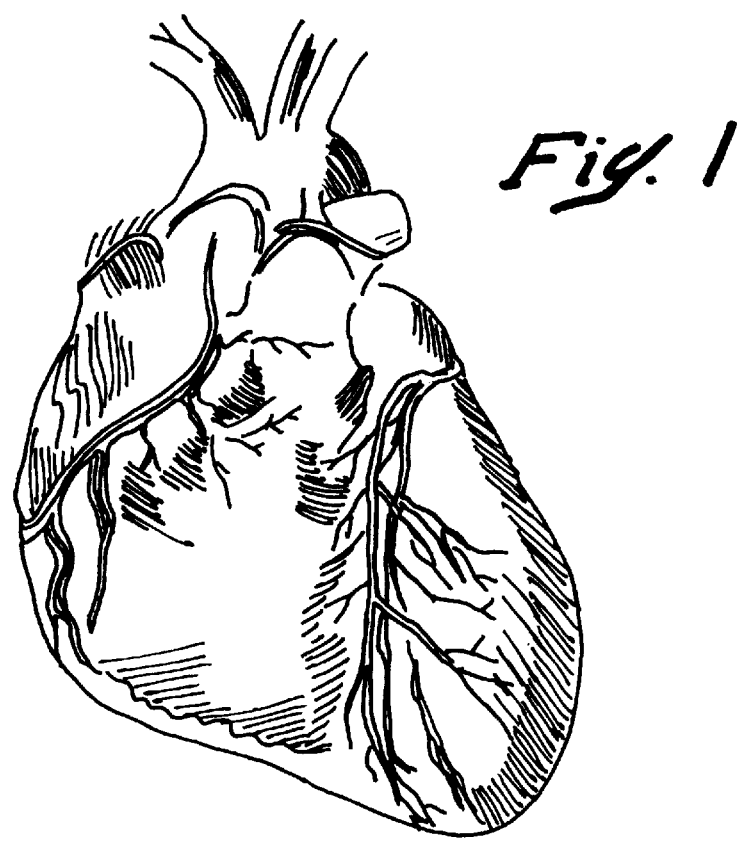
FIG. 1 is a posterior view of the heart.
Figure 2:
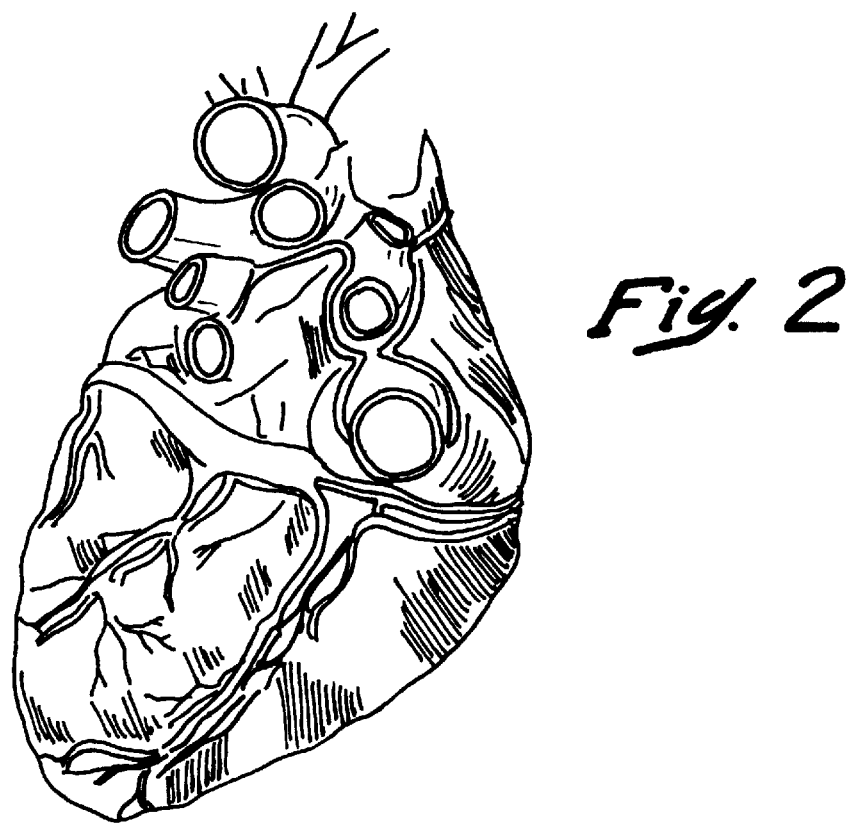
FIG. 2 is an anterior view of the heart.

Having deployed the first cuff-link stent in a location distal of the lesion 12, the stent delivery catheter can be retracted back through the exit opening 22 until fully contained within the lumen 24. Next, the assembly including the guide catheter 18 and the stent delivery catheter can be retracted until the exit opening 22 in the guide catheter resides in the lumen of the artery 10 just opposite the surgically created openings at the location proximal to the stenotic lesion. Now, again, the stent delivery catheter is advanced in the distal direction and is steered out through the exit opening by the diverter plug 36 in the guide catheter. Now, the second stent contained within the delivery catheter is deployed so as to bridge the openings in the arterial and venous walls. When using the above-described method illustrated diagrammatically in FIG. 3, the size of the orifice 37 formed in the stent can be controlled to limit the pressure to which the venous segment will be exposed when coupled in fluid communication with the artery. Moreover, it is necessary to block flow of arterial blood from the vein to the right atrium so that venous pressure/flow remain normal. Thus, an occlusive stent or plug, as at 44, is disposed in the branch of the vein 14 leading back to the right atrium. The presence of the occluding stent will not prevent venous blood from returning to the right atrium for subsequent oxygenation because the heart possesses a highly redundant mechanism called the Thebesian venous system. Earlier studies reported in the literature have shown that if the epicardial Great Cardiac Vein (see FIG. 1) is occluded, coronary venous return drops by only about 15percent.

An alternative approach for performing the PIBS procedure will now be explained with the aid of FIG. 4. Illustrated there is a portion of the myocardium 50 supporting a coronary artery 10' and an adjacent, parallel vein 14'. The arterial segment 10' is shown as having a stenotic lesion 12' partially or fully blocking flow through the artery 12'.

The first step in the procedure would be to enter the coronary artery in a standard fashion, such as by puncturing the femoral artery and introducing a guide wire 16. The guide wire is advanced until its distal end is disposed proximate the lesion 12' and following that, the guide catheter 18 is inserted and routed over or along the guide wire until its outlet port 22 is positioned slightly upstream of the lesion to be bypassed. The catheter 26 carrying a cutting instrument on its distal end is then advanced through the lumen 24 of the guide catheter until its distal end abuts the diverter plug 36 which causes the distal end of the catheter 26 to project outward normal to the guide catheter and against the arterial wall. The distal end of the catheter 26,is made to puncture through both the arterial wall and the adjacent venous wall. The physician will next draw back on the proximal end portion of the catheter 26 until its distal end again is fully contained within the lumen of the guide catheter 18. The guide catheter 18 will -then be advanced through the puncture openings just created and through the lumen of the vein 14' until its outlet port 22 is located just distal of the occlusion 12'. At this point, the catheter 26 will again be advanced so as to project out through the exit port 22 formed through the side wall of the guide catheter and the cutting instrument on the end thereof is again used to create openings through the venous wall and the arterial wall.

Figure 9:
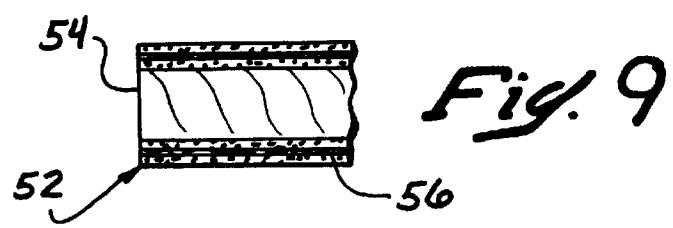
FIG. 9 is a partial cross-sectional view of an alternative stent device.

At this point, the catheter 26 may be removed completely from the lumen 24 and replaced with a stent delivery catheter of known, conventional form. Here, instead of using two small cuff link stents, such as shown in FIGS. 7 and 8, an elongated stent 52 is deployed, such that its proximal end remains in the arterial lumen while the remaining portion of the stent is advanced through the lumen of the vein 14' and with the stent's distal end being brought through the surgically created openings in the vein and artery located just distal of the stenotic lesion 12'. Proximal and distal ends 54, 56 of the stent 52 are desirably radially larger than the remaining tubular portion therebetween, or include cuffs, disks, laps, or flanges as with the cuff-link stents 39 of FIG. 3, to prevent the stent from migrating due to blood flow in the vein 14'. Thus, a single tubular stent, such as is represented in FIG. 4, provides a shunt path around the lesion 12'. As shown in FIG. 9, the stent 52 preferably comprises a braided tubular core 54 which is covered by a fluid impervious layer 56. The inside of the layer.56 is treated so as to encourage endothelial cell growth for stabilizing the stent in place. With the approach shown in FIG. 4, it is no longer necessary to block the venous channel leading back to the right atrium. The interior of the venous conduit 14' is not exposed to arterial blood pressures in that the channel for flow of the arterial blood is through the lumen of the stent device 52.

Figure 10:
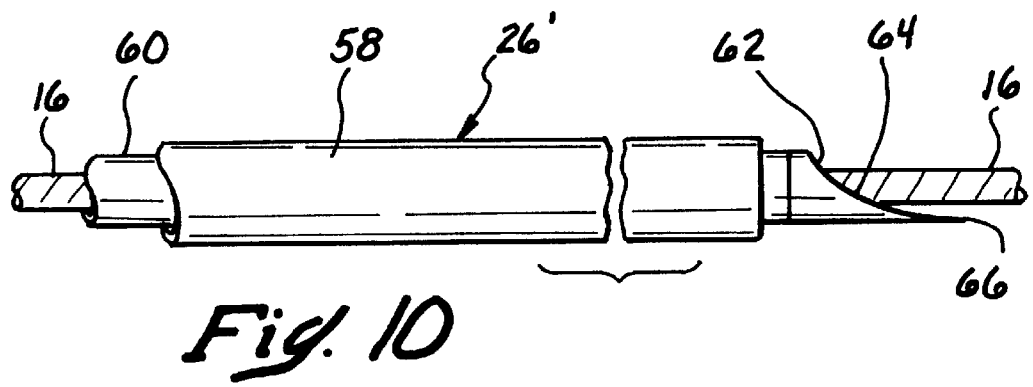
FIG. 10 is a partial side elevation view of an instrument useful in carrying out the method of the present invention.

FIG. 10 illustrates a cutting catheter 26' that uses straight mechanical cutting rather than an electrosurgical approach. It comprises an outer tubular sheath 58 coaxially surrounding an elongated, pushable, torqueable tubular member 60 having a cutting blade 62 affixed to the distal end thereof, the cutting blade also being tubular, but with a tapered leading edge 64 and a pointed tip 66. The tapered edge 64 is beveled to be razor-sharp. Because both the elongated member 60 and the cutting blade 62 are tubular, a guide wire 16 may be used for facilitating the routing of the instrument 26' through the vascular system. During the advancement of the instrument through the vascular system, the blade portion 64 will be fully retracted within the sheath 26' and will only be deployed when properly positioned for cutting through the arterial and venous walls.

FIG. 11 is a partial view of the distal end portion of an electrosurgical cutting instrument. This instrument also comprises an outer tubular sheath 58' having a two conductor cable 68 extending from a. proximal end thereof and with the individual conductors 70 and 72 thereof being brought out and connected respectively to a conductive end cap 28 disposed on the distal end of the sheath 58' and to the needle electrode 30. The needle electrode 30 is preferably retractable through an insulated bushing 74 formed into an aperture in the conductive end cap 28 allowing the needle electrode to be selectively advanced outward from the distal end of the cap 28 without shorting against it.

The needle electrode 30 may comprise an exposed distal metal end portion of an otherwise insulation coated guide wire which may be made to extend out from the end cap 28 on the sheath 58 when it is to be used to perform electrosurgical cutting of the blood vessel walls. Subsequently, however, the guide wire may be extended further in the distal direction through the surgically created openings to be used in guiding the sheath 58' to the distal site and then again used to create the openings through the walls of the vein and artery.

Figure 12:
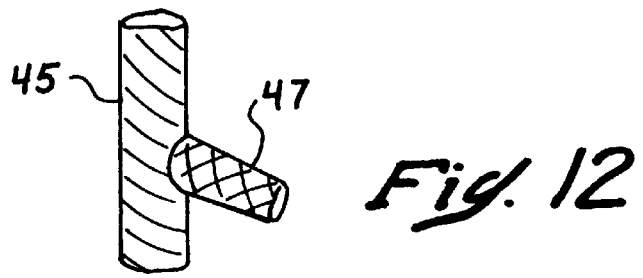
FIG. 12 is a perspective view of a bifurcated stent useful in performing the PIBS procedure.

A bifurcated stent, such as that shown in FIG. 12, may also be used to anastomose the surgically created opening in the arterial and venous walls. In use, the leg 45 may be deployed entirely within the lumen of the artery at a location proximal to the stenotic lesion with the branch 47 extending through the surgically created openings in the arterial and venous wall. Similarly, to anastomose the surgically created openings in the vein and artery walls distal to the stenotic lesion, the leg 45 may be positioned wholly within the lumen of the vein with the branch 47 extending through the surgically created openings.

Figure 13:
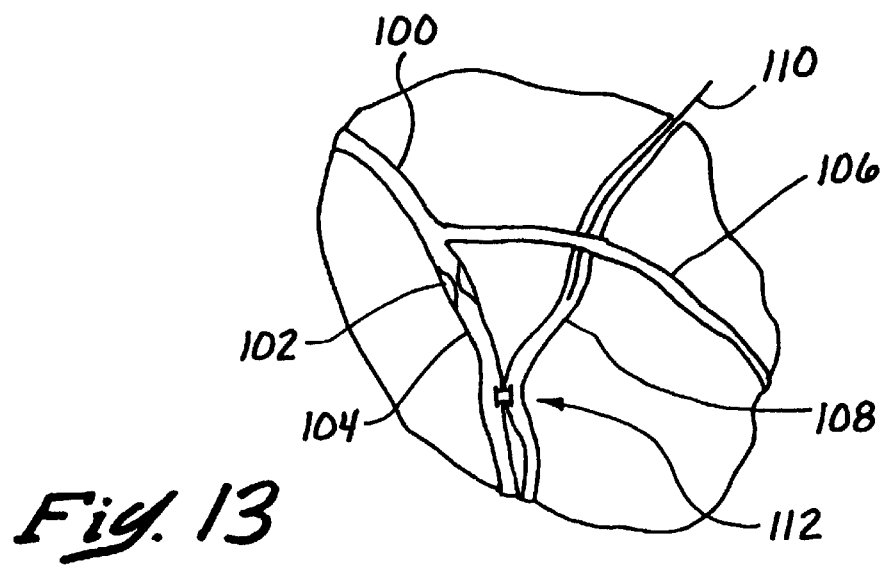
FIG. 13 is an enlarged view of the myocardium showing an alternative variation of the PIBS procedure.

The description of the PIBS procedure set out above presumes the presence of a closely adjacent vein to the artery containing the occlusion to be bypassed. In instances where an occlusion appears at a location in an artery that is spaced some distance from a vein but where an arterial branch proximal to the lesion intersects with a vein that approximates the artery containing the occlusion, the above-described PIBS procedure may be used by puncturing and later anastomosing the arterial branch with the vein at the point of intersection and then joining the vein to the artery distal of the occlusion. In this regard, reference is made to FIG. 13 which is a greatly enlarged view of a portion of the myocardium and illustrating the above-described vein-artery relationship. Here, a coronary artery 100 has a stenotic lesion 102 in a bifurcated branch 104 thereof and proximal to the lesion 102 is another arterial branch 106 that crosses a vein segment 108. By creating an opening in the wall of the arterial branch 106 and the vein 108 at the location of the intersection and anastomosing the two using a stent or otherwise, and then doing the same at a location distal to the lesion 102, an arterial blood supply will be established from the artery 100 through the arterial branch 106 and the vein 108 back to the arterial branch 104 at a location distal of the obstruction 102.

To assist in locating the point of intersection of the arterial branch 106 and the vein 108, a guide wire 110 may be passed down the vein 108. Next, the guide catheter 18 will be routed through the arterial branch 100 and into the branch 106. The guide catheter 18 of FIG. 6 is equipped with a suitable transducer at its distal end capable of sensing its proximity to the metal guide wire 110. The location where the signal output from the transducer is a maximum will pinpoint the location of the intersection and the cutting catheter 26 may then be deployed to create the surgical openings in the arterial branch 106 and the vein 100 which then may be stented. The guide 18 and the cutting catheter 26 may then be routed through that opening and down the vein 108 to a location 112 where the vein and adjacent artery are again punctured and stented. The transducer, for example, may be a Doppler device, an ultrasonic transducer, a Hall effect magnetic transducer, or an rf transmitter that utilizes the guide wire 110 as a receiving antenna.

A catheter for cannulating the coronary sinus, with specific intent for support of stent placement may access the coronary sinus either from the superior vena cava or the inferior vena cava and preferably has a long, more flexible tip of 2 to 5 cms so that it will carefully track as it is advanced into the coronary sinus. It can also be used to track into smaller coronary veins. Since the tip is highly flexible and very soft, it is atraumatic and will gently track either on its own, or over a guide wire.

Also facilitating the PIBS procedure is a coronary venous angiographic catheter that can be used to visualize the coronary venous tree with an injection of a contrast media. Because of retrograde flow, the coronary venous angiographic catheter will preferably have an occlusion mechanism, such as an inflatable balloon on its periphery. With the vein occluded, the contrast media is injected retrograde as the injection is recorded by fluoroscopic imaging.

The PIBS procedure described herein affords numerous advantages over conventional open-heart surgery when performing coronary bypass. The procedure is simple and safe, and even if a difficulty arises during the procedure, the patient is no worse off than prior to the procedure in that the open heart approach is always available as a back-up. The procedure of the present invention is quite simple and can be done with a patient awake and with only a local anesthetic used at the point of percutaneous entry. The hospital stay could conceivably be reduced to a single day and the period for full recuperation is significantly less than is required when open heart surgery is employed. Further, the procedure is independent of lesion morphology and can be used with total occlusions, diffuse or long lesions and other high risk or dangerous morphologies. By limiting the pressure in the veins, they can expected to function naturally. The my r epicardial arteries always have a corresponding vein very close by, making the procedure practical.

What is claimed is:

1. A method for percutaneous, in-situ coronary bypass in a a lesion located in a coronary artery of a mammalian patient, said method comprising the steps of:

(A) providing a flexible catheter which has a tissue piercing instrument passable therefrom;

(B) inserting said catheter into the vasculature and positioning at a first location within a coronary blood vessel;

(C) passing the tissue piercing instrument from the catheter to form a blood flow path between the coronary artery proximal to the lesion and a coronary vein;

(D) repositioning the catheter at a second location within a coronary blood vessel; and, (E) passing the tissue piercing instrument from the catheter a second time to form a second blood flow path between the coronary artery distal to the lesion and said coronary vein.

2. The method of claim 1 further comprising the step of:

(F) placing a blocking stent in said coronary vein proximal to the proximal blood flow path formed in Step C.

3. The method of claim 1 further comprising the step of:

(F) placing an elongated stent such that it extends through the blood flow paths created in Steps C and E and through the segment of said vein between said blood flow paths.

4. The method of claim 3 wherein the stent placed in step F comprises:

a braided tubular core covered by a fluid impervious layer.

5. The method of claim 4 wherein the fluid impervious layer of the stent is treated to encourage endothelial cell growth.

6. The method of claim 3 wherein the stent placed in Step F is configured to carry arterial blood in one direction through said segment of said coronary vein while allowing venous blood to naturally flow in the other direction through said segment of said coronary vein.

7. A stent for use in an in-situ arterial bypass, the bypass extending from the lumen of an artery, through a first opening in an artery wall, through the lumen of an adjacent vein and into the lumen of an artery through a second opening in an artery wall, the stent comprising:

an elongate, flexible tubular member having an interior surface, an exterior surface, a first end, a second end, and a hollow interior passage extending therethrough from the first end to the second end, the first and second ends being sized to engage the first and second artery wall openings and prevent longitudinal movement of the stent following implantation and the portion of the stent that extends between its first and second ends being sized relative to the diameter of the vein lumen such that arterial blood will be channeled through the stent in a direction opposite normal venous flow and venous blood will be permitted to flow through the vein lumen, past the stent, in the direction of normal venous flow.

8. The stent of claim 7, wherein cuffs are provided on the first and second ends of the tubular member.

9. The stent of claim 7, wherein disks are provided on the first and second ends of the tubular member.

10. The stent of claim 7, wherein laps are provided on the first and second ends of the tubular member.

11. The stent of claim 7, wherein flanges are provided on the first and second ends of the tubular member.

12. The stent of claim 7, wherein the tubular member comprises a braided tubular core covered by a fluid impervious layer.

13. The stent of claim 12, wherein the fluid impervious layer is treated so as to encourage endothelial cell growth thereon.

14. The stent of claim 12, wherein the first and second ends of the tubular member are selected from the group of structures consisting of:

a disk structure;

a cuff structure;

a lap structure; and a flange structure.

15. The stent of claim 7, wherein the tubular member has a diameter that is smaller than the diameter of the lumen of the vein such that venous blood is permitted to flow through the vein when the stent is in the bypass position.

16. The stent of claim 15, wherein the first and second ends of the tubular member are selected from the group of structures consisting of:

a disk structure;

a cuff structure;

a lap structure; and a flange structure.

* * * * *